(12) United States Patent
Churovich

(10) Patent No.: US 10,969,572 B2
(45) Date of Patent: Apr. 6, 2021

(54) ELECTRONIC VISUAL FOOD PROBE

(71) Applicant: Douglas D. Churovich, Des Peres, MO (US)

(72) Inventor: Douglas D. Churovich, Des Peres, MO (US)

(*) Notice: Subject to any disclaimer, the term of this patent is extended or adjusted under 35 U.S.C. 154(b) by 68 days.

(21) Appl. No.: 15/592,476

(22) Filed: May 11, 2017

(65) Prior Publication Data

US 2017/0329125 A1  Nov. 16, 2017

Related U.S. Application Data

(60) Provisional application No. 62/334,794, filed on May 11, 2016.

(51) Int. Cl.
| | |
|---|---|
| *G02B 23/24* | (2006.01) |
| *G01K 1/14* | (2006.01) |
| *H04N 5/225* | (2006.01) |
| *G01K 1/02* | (2021.01) |
| *G01N 33/12* | (2006.01) |

(52) U.S. Cl.
CPC .......... *G02B 23/2492* (2013.01); *G01K 1/02* (2013.01); *G01K 1/14* (2013.01); *G01N 33/12* (2013.01); *G02B 23/2469* (2013.01); *G02B 23/2484* (2013.01); *H04N 5/2256* (2013.01); *G01K 2207/06* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 4,260,261 A | 4/1981 | Mann et al. | |
| 4,699,463 A | 10/1987 | D'Amelio et al. | |
| 4,837,615 A | 6/1989 | Boshier | |
| 4,849,626 A | 7/1989 | Franklin, Jr. | |
| 5,060,063 A | 10/1991 | Freeman | |
| 6,111,599 A | 8/2000 | Nance et al. | |
| 6,277,066 B1 | 8/2001 | Irwin | |
| 6,580,449 B1 | 6/2003 | Meltzer | |
| 8,169,477 B2 | 5/2012 | Tawfiq et al. | |
| 10,149,958 B1 * | 12/2018 | Tran ....................... | G16H 20/30 |

(Continued)

FOREIGN PATENT DOCUMENTS

| | | |
|---|---|---|
| CA | 2618344 A1 | 7/2008 |
| EP | 1 949 877 B1 | 6/2012 |

(Continued)

*Primary Examiner* — Talha M Nawaz
(74) *Attorney, Agent, or Firm* — Sandberg Phoenix and von Gontard

(57) ABSTRACT

An electronic visual food probe for viewing the interior of a body of food being cooked. The probe has a food-safe, heat resistant and elongated stem designed for insertion into the body of food. A thermally insulated cavity formed in one end of the stem has a window that allows light into and out of the cavity. A light source illuminates the interior of the food exposed to the window. An electronic image sensor receives the light reflected from the interior surfaces of the food proximate the window and generates an elongated color image of the reflected light. An electronic display system receives the elongated color image from the image sensor and displays it on an electronic display for viewing.

20 Claims, 3 Drawing Sheets

(56) References Cited

U.S. PATENT DOCUMENTS

| | | | |
|---|---|---|---|
| 2008/0159653 A1* | 7/2008 | Dunki-Jacobs | A61B 1/04 |
| | | | 382/293 |
| 2008/0228072 A1* | 9/2008 | Nycz | A61B 5/05 |
| | | | 600/437 |
| 2012/0323089 A1* | 12/2012 | Feer | A61B 5/01 |
| | | | 600/301 |
| 2014/0213850 A1* | 7/2014 | Levy | A61B 1/00137 |
| | | | 600/156 |
| 2015/0055133 A1 | 2/2015 | Egalon | |
| 2015/0126873 A1* | 5/2015 | Connor | A61B 5/4866 |
| | | | 600/475 |
| 2016/0112684 A1* | 4/2016 | Connor | A61B 5/1114 |
| | | | 348/158 |
| 2016/0317060 A1* | 11/2016 | Connor | A61B 5/14532 |
| 2017/0312614 A1* | 11/2017 | Tran | A61B 5/11 |
| 2018/0149519 A1* | 5/2018 | Connor | G01J 3/0256 |
| 2020/0020165 A1* | 1/2020 | Tran | G06N 7/005 |
| 2020/0152312 A1* | 5/2020 | Connor | G16H 40/67 |

FOREIGN PATENT DOCUMENTS

| | | |
|---|---|---|
| WO | 8705462 A2 | 9/1987 |
| WO | 2005099460 A1 | 10/2005 |

* cited by examiner

ELECTRONIC VISUAL FOOD PROBE

CROSS REFERENCE TO RELATED APPLICATIONS

This application claims priority to U.S. App. No. 62/334,794 filed May 11, 2016, which is entitled "Digital Visual Food Probe" and which is incorporated herein by reference.

STATEMENT REGARDING FEDERALLY SPONSORED RESEARCH OR DEVELOPMENT

Not applicable.

BACKGROUND OF THE INVENTION

This invention relates generally to an electronic apparatus to facilitate the viewing of a sliver or length of a portion of food such as, for example, the visual sampling of the interior of a piece of cooked meat, and more particularly to a novel electronic probe that generates a substantially accurate visual image of the coloration of an interior sliver or length within a piece of cooked meat in a single scan for determination of sufficient level of cooking.

It is often desirable when cooking or grilling foods, and in particular when grilling meats, to determine whether the meat has been cooked sufficiently in the interior or body of the meat being cooked. One well-recognized method to determine the extent to which the interior or body of a piece of meat has been cooked is to measure or monitor the internal temperature of the item. This may entail a simple temperature measurement at a single location in the body of the piece of meat, or may be more complex, such as for example obtaining multiple temperature measurements and/or monitoring at one or multiple locations in the body of the piece of meat and/or at various depths in the body or interior of the piece of meat. It is also often desirable to determine the interior temperatures while the meat is still being cooked. That is, it is often desirable to be able to measure the meat's interior temperature without removing the food meat from its cooking environment, such as an oven or grill.

Not surprisingly, a wide variety of devices exist in the art that can determine the temperature of a piece of cooked meat. These devices may comprise a single or multiple temperature probes coupled with analog or digital readouts or displays, and may operate on mechanical or electronic principles, and can incorporate other various features such as for example, a separate probe and temperature display, rechargeable batteries, an elongated handle or grip, or a backlight display. However, temperature probes do not provide the ability to visually scan the interior of the cooked piece of meat.

Often, in addition to determining the interior temperature of a cooked piece of meat, it is desirable to examine the coloration of the interior of the meat to more accurately ascertain the distribution of the degree of cooking the piece of meat has attained. This has traditionally been accomplished by slicing into the meat while still in the cooking environment with a knife or other utensil to open the meat's interior for a visual inspection, or first removing the piece of meat from the cooking environment and then slicing into the meat with a knife or other utensil to open the meat's interior to view. Of course, cutting and viewing the meat while still in its cooking environment is difficult and uncomfortable at the least, and potentially dangerous at the worst in exposing the person cooking the meat to extremely high heat, searing heated metal, and open flames. In addition, this traditional technique has the undesirable result of marring the meat prior to presentation and consumption. Further, whether in the cooking environment or after being removed from the cooking environment, slicing or cutting the meat exposes those portions of the meat to the low temperature environment prematurely, which results in discoloration and less appeal, and can lead to the determination that additional cuts or slices or cooking may be warranted.

It would therefore be desirable to have a device or apparatus that can readily and accurately discern and display the coloration of the interior of a cooked or cooking piece of meat (or a body of some food type other than meat) without requiring that the meat (or a body of some food type other than meat) be sliced open for visual inspection. In addition, it would be further desirable for such a device to be able to quickly and accurately discern and display the coloration of the interior of a cooked or cooking piece of meat (or a body of some food type other than meat) without removing the meat (or a body of some food type other than meat) from the cooking environment. As will become evident in this disclosure, the present invention provides such benefits over the existing art.

BRIEF DESCRIPTION OF THE DRAWINGS

The illustrative embodiments of the present invention are shown in the following drawings which form a part of the specification.

Corresponding reference characters indicate corresponding parts throughout the several views of the drawings.

DETAILED DESCRIPTION

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
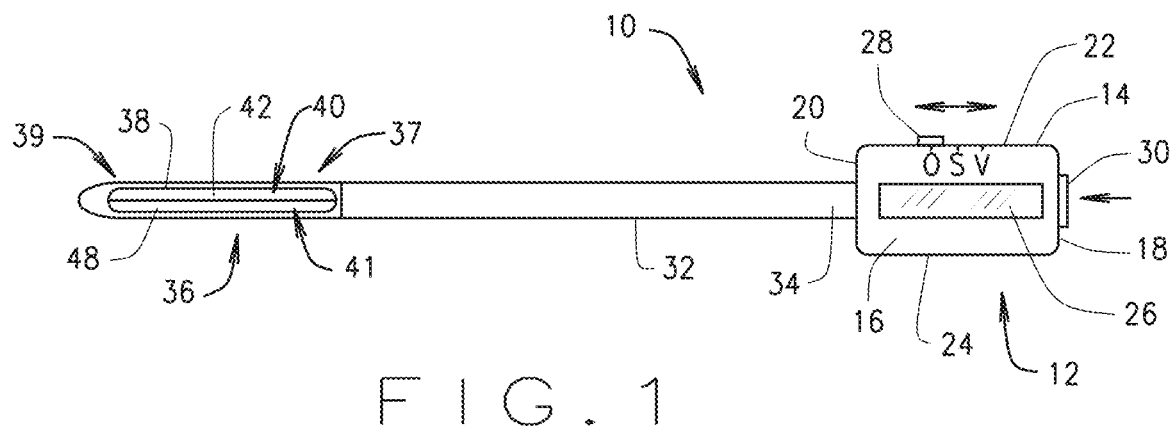
FIG. 1 is a top view of a first representative embodiment of an electronic visual food probe incorporating features of the present invention.
Figure 2:
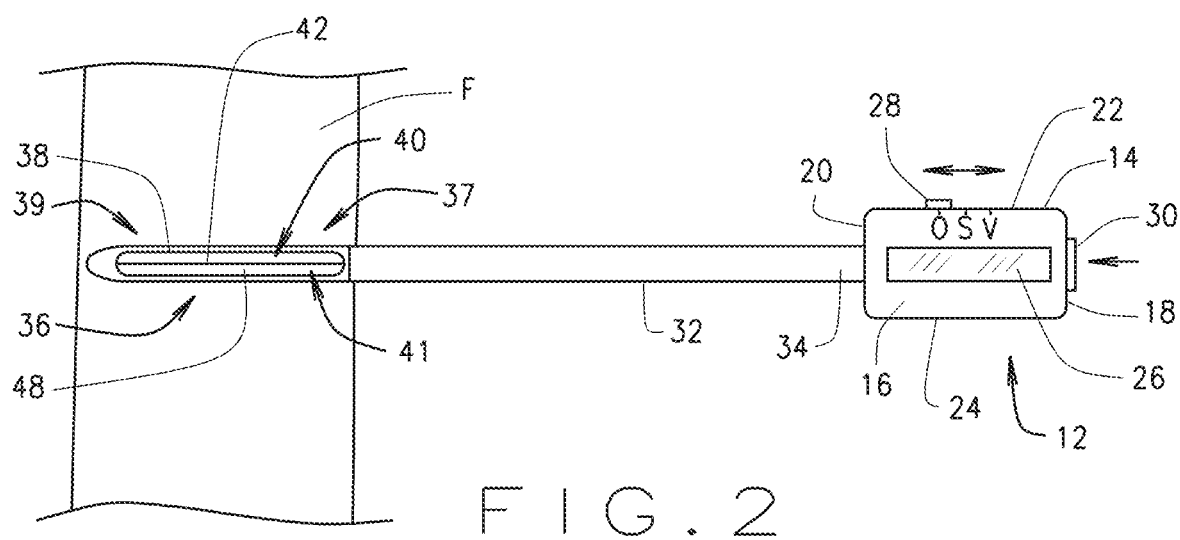
FIG. 2 is the top view of the first representative embodiment of FIG. 1, with the stem of the probe partially inserted into a piece of meat.

In referring to the drawings, a first representative embodiment of the novel electronic visual food probe 10 of the present invention is shown generally in FIG. 1, where the present invention is depicted by way of example, and in FIG. 2, where the present invention is depicted by way of example inserted into a body of food F. In this first representative embodiment, the food probe 10 comprises an electronic display system 12 contained in a slightly flattened box-shaped handle 14, having dimensions of approximately one inch wide by two inches long by ½ inch deep. The handle 14 has a generally rectangular face 16, a first end 18, a second end 20 parallel to and opposite the first end 18, a first side 22 and a second side 24 parallel to and opposite the first side 22. A flat digital color display 26 is positioned generally in the center of the outer surface of face 16 of the handle 14. A three-position mode switch 28 is positioned on the first side 22 of the handle 14, and an activation button switch 30 is positioned on the first end 18 of the handle 14. Of course, the configuration, shape and dimensions of the handle 14 are not limited to these particular specifications, but can vary substantially for a variety of reasons, including without limitation, aesthetic considerations, ability to house various shapes and sizes of components in the handle 14.

An elongated, rigid, substantially uniform tubular stem 32, having a proximal end 34 and a distal end 36, the stem 32 extends at its proximal end 34 from the second end 20 of the handle 14, where the stem 32 is rigidly attached to the handle 14. From its distal end 36 to its interface with the electronic display system 12, the stem 32 defines an inner cavity 37. A seal 37A seals the upper end of the cavity 37 inside the stem 32 proximate the interface between the optic lenses 42 and 48 and their respective optic cables 44 and 50 by a 37A, in order to prevent the intrusion of moisture, food components or other such undesirable material, such that the cavity 37 and stem 32 form a housing 39 for the optic lenses 42 and 48. The seal 37A is formed of a solidified liquid sealant material injected into the area above the optic lenses 42 and 48. Of course, the cavity 37 can be filled with one or more materials and fixtures to positionally secure various components within the cavity 37, including for example, various adhesives, tapes, and mounting brackets. Alternately, the cavity 37 and the housing 39 can be part of a separate component that can be attached to the stem 32 (not shown). The stem 32 is approximately eight inches long, has an outer diameter of preferably less than one-fourth inch, and has a translucent or transparent and generally straight elongated window 38 near its distal end 36. The window 38 has a width of approximately one fourth the circumference of the stem 32, and extends from a position near the tip of the distal end 36 of the stem 32 approximately two inches toward the proximal end 34. The length of the stem 32 having the window 38 may be referred to as the imaging section of the probe 10.

The stem 32 encases two light transmitting conduits, 40 and 41. The light transmitting conduit 40 comprises a first elongated optic lens 42, a first fiber optic cable 44 and a light-emitting-diode ("LED") array 46. The first optic lens 42 is secured inside the stem 32 behind the window 38 and connects to the first fiber optic cable 44. The first fiber optic cable 44 then extends up through the stem 32 and into the handle 14, where it connects to the LED array 46 housed therein. The first optic lens 42, the first fiber optic cable 44 and the LED array 46 are interconnected and configured such that when the LED array 46 is activated, the light so generated will travel through the first fiber optic cable 44 and into the first optic lens 42. The optic lens 42 receives the LED light from the optic cable 44 and redirects the light to a direction perpendicular to and away from the central axis of the tubular handle 14 and in a dispersed length such that the light generated by the LED array 46 exits the window 38 along substantially the full length of the window 38 and spreads radially outward relative to the central axis of the tubular handle 14. As can be appreciated, light generated by the LED array 46 can thereby be directed to the inner surface of a body of food F or meat adjacent the window 38 when the distal end 36 of the stem 32 is inserted in the body of food F.

The light transmitter conduit 41 comprises second elongated optic lens 48, a second fiber optic cable 50 and a digital image sensor 52. The second optic lens 48 is secured inside the stem 32 behind the window 38 generally parallel to the first optic lens 42, and connects to the second fiber optic cable 50. The second fiber optic cable 50 then extends up through the stem 32 and into the handle 14, where it connects to the digital image sensor 52. The second optic lens 48, the second fiber optic cable 50 and the digital image sensor 52 are interconnected and configured such that light entering the second optic lens 48 from the window 38 in the stem 32 travels through the second optic lens 48, is directed at a right angle up and through the second fiber optic cable 50, and to the digital image sensor 52. The digital image sensor 52 collects a color image created by the light from the second fiber optic cable 50 that has been reflected by portions of the body of food F exposed to the window 38, and converts the image into electronic data representative of the color image of the interior of the body of food F (such as meat) thus received. The second optic lens 48 collects light from substantially the full length of the window 38. Thus, as can be understood, when the distal end 36 of the stem 32 is inserted into a body of food F (such as a cooked piece of meat) the fiber probe 10 creates a long and thin electronically displayable image of the coloration of the interior portion of that food item along the length of the window 38 in the stem 32.

Figure 8:
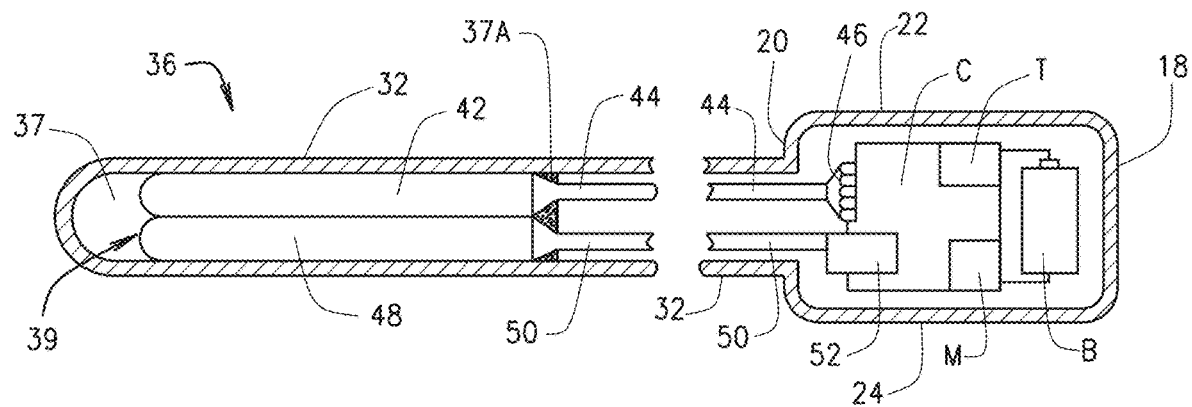
FIG. 8 is a split cut-away top view of the first representative embodiment of the electronic visual food probe of FIG. 1.

Referring now to FIG. 8, a small computer processor C is housed in the handle 14 and acts as an electronic data converter to convert the images generated by the digital image sensor 52 into electronic still or video data files. The computer processor C stores these electronic files in a digital memory unit M attached to the computer processor C in the handle 14, and displays the image on the flat digital color display 26. A small replaceable battery B, housed in the handle 14, provides electronic power to operate the electronic components of the probe 10.

The three-position mode switch 28 allows a user to select between three modes: (i) OFF, which deactivates the probe 10 electronic components; (ii) PHOTO, which only allows the probe 10 to take instantaneous photo, or "still" shots of the interior of the food being probed; and (iii) VIDEO, which allows the probe 10 to act as a video camera. The button switch 30 activates the camera functions of the probe 10. That is, when the distal end 36 of the stem 32 is inserted into a body of food (such as a cooked piece of meat), and when the three-position mode switch 28 is in the PHOTO position, the probe 10 will take a "still" image of the interior of the food (such as cooked meat) along the length of the window 38 of the stem 32 when the button switch 30 is depressed as shown in FIG. 1. Similarly, when the distal end 36 of the stem 32 is inserted into a body of food (such as a cooked piece of meat), and when the three-position mode switch 28 is in the VIDEO position, the probe 10 will take a "video" image of the interior of the food (such as cooked meat) along length of the window 38 of the stem 32, starting when the button switch 30 is first depressed and stopping when the button switch 30 is depressed a second consecutive time. These images, whether still or video, are stored in the digital memory unit M and displayed on the flat digital color display 26.

As can be appreciated, the displayable images generated by the probe 10 are elongated and relatively thin strip- or sliver-shaped to correspond to the same-shaped portions of the body of food F or cooked meat adjacent the window 38. Accordingly, the displayable images will have a length substantially longer than the average width of the distal end 36 of the stem 32, such as for example a length that is at least twice the average width of the distal end 36 of the stem 32. Of course, the length of the displayable images may be three, four, five or even more, greater than the average width of the window 38 and/or the distal end 36 of the stem 32. Such elongated displayable images generated by the probe 10 provide a spectrum view of the interior portion of the body of food F adjacent the window 38. Hence, inserting the imaging section of the stem 32 in a generally perpendicular fashion into a one inch thick meat steak (see, e.g., FIG. 2) will allow the probe 10 to quickly generate an accurate sliver-shaped color-indicative or colored displayable image on the digital color display 26 that spans the full width of the interior of the steak. This provides the user with a quick and accurate visual check on the degree to which the steak has been cooked, or the "doneness" of the steak, and an actual representation of the color spectrum of the meat across the entire width of the steak at the point of insertion of the probe 10.

Preferably, the entire probe 10 is constructed of materials that are physically rugged, food-safe (usable for contact with food products and goods without causing harm to the food or the consumer of the food), and can withstand the heat from cooking environments, up to and including the heat generated by open flames, such as for example a fire pit or BBQ grill, such that the food probe 10 can function properly and safely in such environments and under such conditions. However, the probe 10 can be constructed such that just the stem 32 and the window 38 comprise materials that are physically rugged, food-safe, and can thermally insulate the cavity 37 from the heat generated by cooking, including the heat generated by open cooking flames, such as those generated in a barbeque grill, fire pit, oven or stove. Such temperatures may for example be as low as 200 degrees Fahrenheit, or may be higher, including various temperatures across the range of 200 degrees Fahrenheit to 600 degrees Fahrenheit, or even higher. The term "food-safe" meaning that the material can be used in conjunction with the preparation and serving of food items for human consumption.

Figure 3:
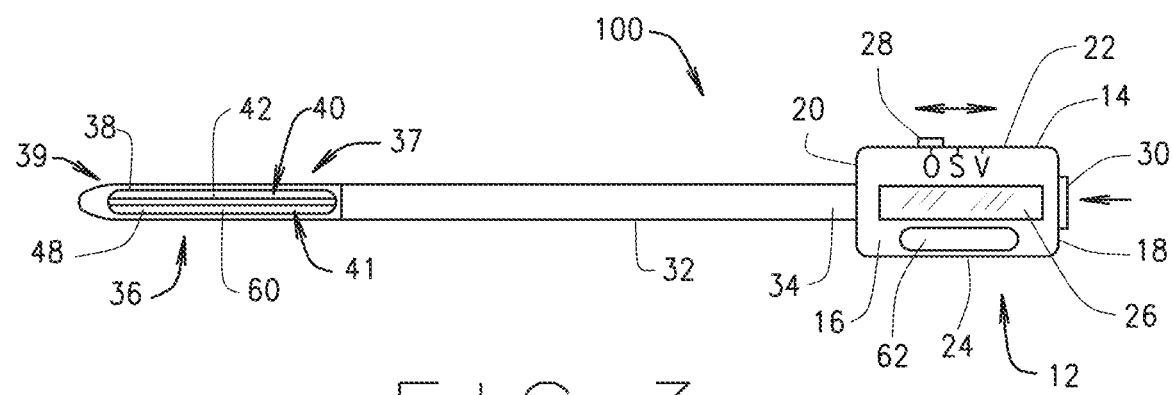
FIG. 3 is a top view a second representative embodiment of an electronic visual food probe incorporating features of the present invention.

A second embodiment 100 of the present invention is shown in FIG. 3. In the embodiment of the probe 100, a temperature sensor 60 is positioned in the stem 32 next to the second optic lens 48 in the vicinity of the window 38. The temperature sensor 60 measures the temperature of the body of food F in proximity to the window 38 and generates an electronic signal indicative of the temperature so measured. The temperature sensor 60 is connected by wire through the stem 32 and into the electronic display system 12 to connect to the computer processor C. The computer processor C receives the electronic signal from the temperature sensor 60, converts the signal into an electronic display signal indicative of the temperature measured by the sensor 60, and generates a display on a second LCD display 62 as readable characters in degrees Fahrenheit and Centigrade indicative of the temperature measured by the temperature sensor 60.

Figure 4:
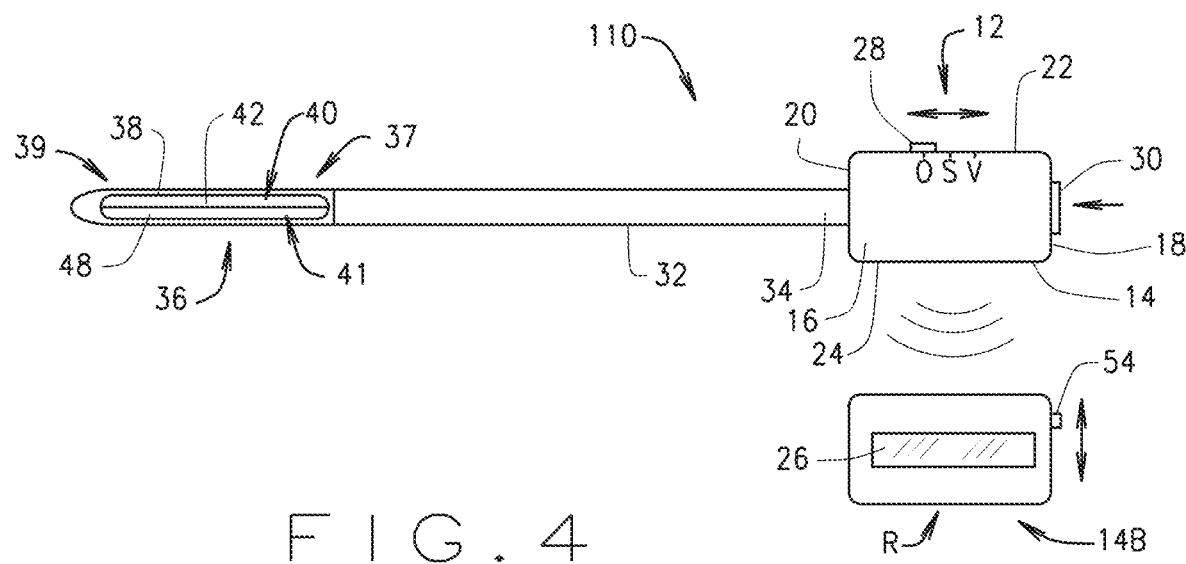
FIG. 4 is a top view a third representative embodiment of an electronic visual food probe incorporating features of the present invention.

A third embodiment 110 of the present invention is shown in FIG. 4, where the digital color display 26 is separated from the handle 14 and positioned in a housing component 14B. The handle 14 connects to the stem 32 and houses the computer processor C and memory unit M. In addition, an electronic wireless transmitter T housed in the handle 14 (see FIG. 8) transmits the electronic data indicative of the color image generated by the image sensor 52 from the memory unit M or alternately the computer processor C to an electronic wireless receiver R (not shown) in the housing component 14B. The wireless receiver R then communicates the electronic data to the flat digital color display 26, where the displayable image is displayed. A slidable ON/OFF switch 54 activates and deactivates the digital color display 26 of the housing component 14B.

Figure 5:
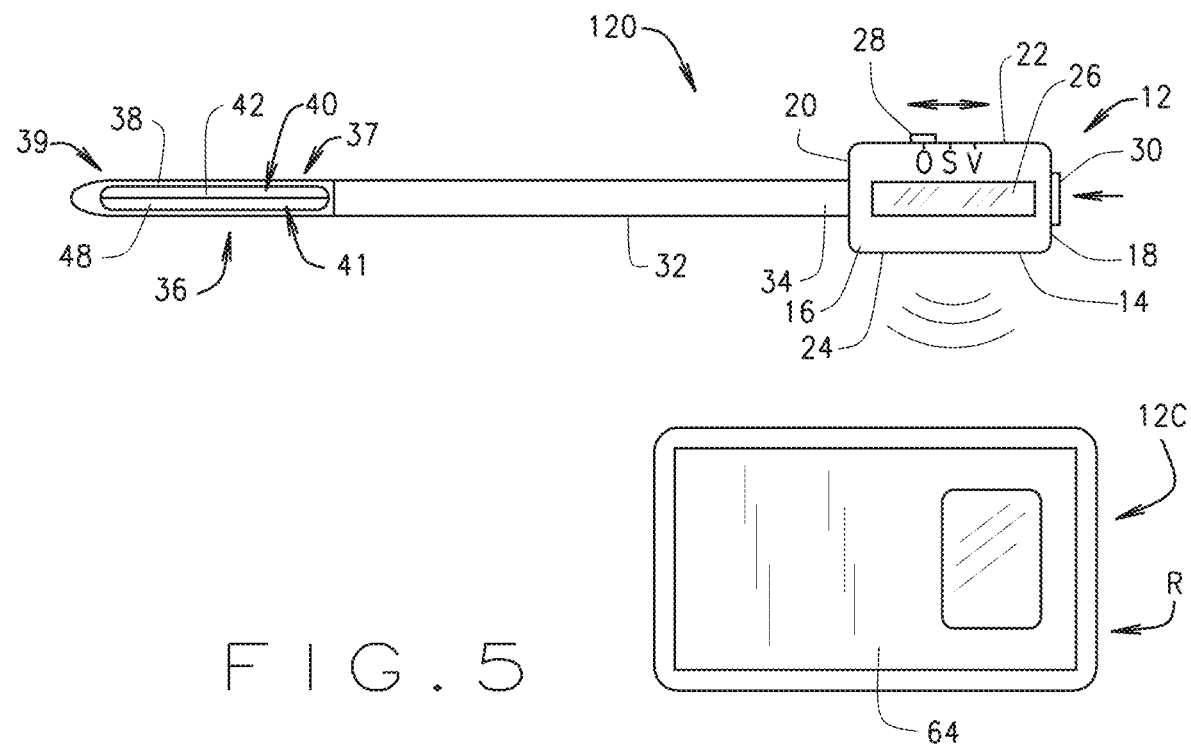
FIG. 5 is a top view a fourth representative embodiment of an electronic visual food probe incorporating features of the present invention.

A fourth embodiment 120 of the present invention is shown in FIG. 5, in which the handle 14 of the probe 120 communicates with a personal data device 12C, such as for example a personal computer, a laptop computer or tablet device, a cellular telephone, a "Bluetooth" capable device or electronic component, or other similar device having a digital display 64, to display the displayable image from the image sensor 52.

In this fourth embodiment, handle 14 connects to the stem 32 and houses the computer processor C and memory unit M. In addition, an electronic wireless transmitter T (not shown, but housed in the handle 14) transmits the electronic data indicative of the color image generated by the image sensor 52 from the memory unit M or alternately the computer processor C to an electronic wireless receiver R (not shown) housed in a personal data device such as for example the cellular telephone 12C. The personal data device 12C receives the electronically captured image from the memory unit M or the computer processor C and generates the image on the digital display 64 of the device 12C. The personal data device 12C can also store or otherwise utilize or manipulate the electronic data received from the wireless transmitter T as determined by the software stored in and accessible for use on the device.

Figure 6:
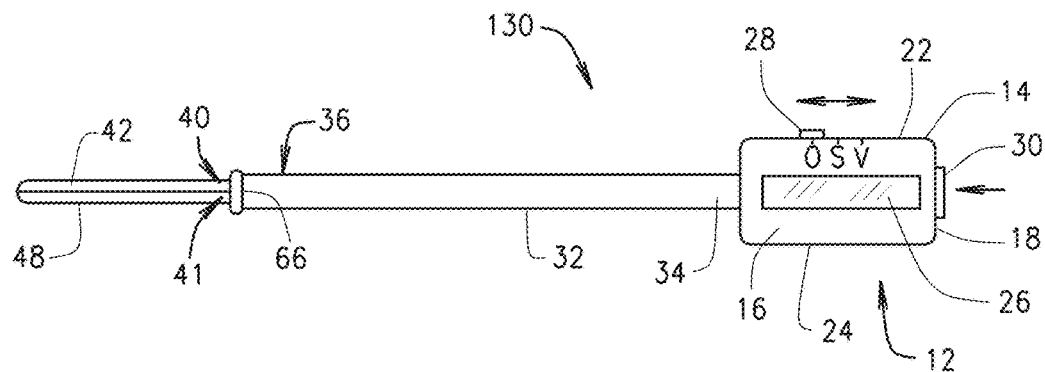
FIG. 6 is a top view a fifth representative embodiment of an electronic visual food probe incorporating features of the present invention.

A fifth embodiment 130 of the present invention is shown in FIG. 6. Here, the stem 32 does not extend the full length of the probe 130. Rather, the light transmitting conduits 40 and 41 are rigidly attached to and extend out of the distal end 36 of the stem 32. A high temperature seal 66 at the interface between the conduits 40, 41 and the distal end 36 of the stem 32 prevents moisture, food components or other such undesirable materials from entering the stem 32. Consequently, the light transmitting conduits 40 and 41, and their respective first and second first optic lenses 42 and 48, must be physically rugged, food-safe, and can withstand the heat generated by cooking, including the heat generated by open cooking flames, such as those generated in a barbeque grill, fire pit, oven or stove. In addition, one or more of the light transmitting conduits 40 and 41 and their respective first and second first optic lenses 42 and 48 must be substantially rigid. Further, there is no window 38 through which the first and second first optic lenses 42 and 48 must view the food being probed. Of course, the stem 32 can be solid or otherwise filled so as to eliminate the need for the seal 66.

Figure 7:
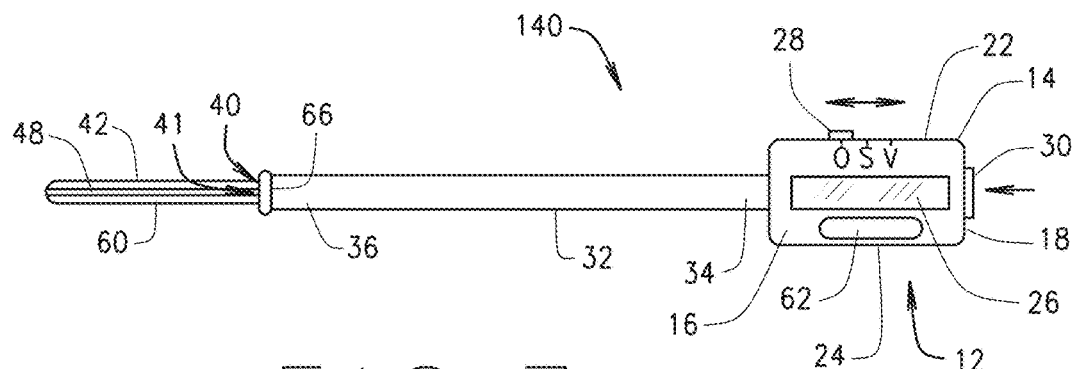
FIG. 7 is a top view a sixth representative embodiment of an electronic visual food probe incorporating features of the present invention.

A sixth embodiment 140 of the present invention is shown in FIG. 7. As in the embodiment 130 of FIG. 6, the stem 32 does not extend the full length of the probe 140. Rather, the light transmitting conduits 40 and 41 are rigidly attached to and extend out of the distal end 36 of the stem 32. Yet, in addition, the temperature probe 60 of embodiment 100 of FIG. 3, is also rigidly attached to and extends out of the distal end 36 of the stem 32. The high temperature seal 66 at the interface between the light transmitting conduits 40 and 41 and the temperature probe 60, and the distal end 36 of the stem 32 prevents moisture, food components or other such undesirable materials from entering the stem 32. Consequently, the light transmitting conduits 40 and 41 and their respective first and second first optic lenses 42 and 48, and the temperature probe 60, must all be physically rugged, food-safe, and can withstand the heat generated by cooking, including the heat generated by open cooking flames, such as those generated in a barbeque grill, fire pit, oven or stove. In addition, one or more of the light transmitting conduits 40 and 41, the first and second first optic lenses 42 and 48, and the temperature probe 60, must be substantially rigid. Again, there is no window 38 through which the first and second first optic lenses 42 and 48 must view the food being probed.

While I have described in the detailed description several configurations that may be encompassed within the disclosed embodiments of this invention, numerous other alternative configurations, that would now be apparent to one of ordinary skill in the art, may be designed and constructed within the bounds of my invention as set forth in the claims. Moreover, the above-described novel mechanisms of the present invention, shown by way of example at 10, 110, 120, 130 and 140 can be arranged in a number of other and related varieties of configurations without departing from or expanding beyond the scope of my invention as set forth in the claims, such as for example making insubstantial changes to the dimensions of the probe components.

For example, the first fiber optic cable 44 and the second fiber optic cable 50 can each be constructed of a single cable, a bundle of cables or a collection of spliced cables. Also, it is not necessary that the light source for the probe 10 be an LED array, such as at 46, but can alternately be for example a light bulb, a single LED, a laser emitter, or any of a myriad of other electronic light emitting sources. Further, the first light transmitting conduit 40 can, for example, alternately be replaced with an LED array 46 (or other electronic light source) positioned in the window 38. Similarly, the second light transmitting conduit 41 can be replaced with a system in which the electronic image sensor 52 is positioned in the window 38, and transmits the electronic images to the computer C either through a wire or set of wires, a cable, a hard network, or wirelessly.

Also, while preferable, it is not necessary for the stem 32 to be uniformly tubular or cylindrical. Rather, the stem 32 can be configured with a wide variety of cross-sectional shapes and sizes, so long as the stem 32 is capable of performing its allocated functions as described herein. Similarly, it is not necessary that the stem 32, the cavity 37 or the housing 39 extend in a straight and perpendicular fashion from the handle 14. Rather, any one or more of these components can be a myriad of various shapes and sizes, and can extend from the handle 14 in any of a variety of configurations, so long as the stem 32 and the imaging components can be inserted into the body of food F.

By way of further example, the stem 32 can be a variety of lengths, so long as the stem 32 has an imaging section that can be inserted into the food or meat. Likewise, the window 38 can be a variety of lengths, widths and shapes, so long as the window 38 provides the function of enabling the probe 10 to visually view and generate a displayable image indicative of the interior of a food item proximate the window 38 which is preferably a color image. While the probe 10 is operated by an internal battery B, any variety of appropriate power sources, such as for example a solar power array or an AC power cord, can be utilized to power the probe 10.

In addition, the digital color display 26 can be configured in any of a wide variety of shapes and sizes, so long as the digital color display 26 is capable of generating an electronically displayable image that substantially mimics or otherwise accurately indicates the coloration of the interior of the food product being probed.

Of course, the probe 10 need not operate with a computer C or a memory unit M, but can utilize other similar electronics, so long as such electronics provide the utility of enabling the probe 10 to take a color image from the interior of a body of food F and generate a replicated representative color image on a display, such as the digital color display 26.

Moreover, the light transmitting conduit 40 and 41 can comprise a wide variety of configurations. For example, the optic lenses 42 and 48 can be a variety of differing shapes and sizes, and in particular can be longer or shorter or wider or thinner than depicted, or can be oriented differently within the cavity 37, so long as the lens 42 is capable of dispersing light from the LED array 46 through the window 38 in a manner to effectuate the function of the probe 10. Further, the optic lenses 42 and 48 can be through lenses that allow the passage of light through the body of the lens. Alternately, the lenses 42 and 48 can be replaced with a reflective surface that merely change the direction of the light, such as for example a mirrored surface that directs light from the LED array 46 through the window 38 (for the transmitting conduit 40), or that directs light reflected from the body of food F through the window 38 and upward into the optic cable 50 (for the transmitting conduit 41). Of course, the LED array 46 can be attached to the optic cable 44, and the image sensor 52 can be attached to the optic cable 50, in a number of ways well understood in the art, including for example, optic adhesives and optic fittings. In addition, the LED array 46 and the image sensor 52 need not be positioned in the handle 14. Rather, either or both of the LED array 46 and the image sensor 52 can be positioned wholly or at least in part in the cavity 37 or in the housing 39, or alternatively anywhere along the length of the stem 32, or even outside (at least in part) the stem 32, the cavity 37 and/or the housing 39.

Additional variations or modifications to the configuration of the novel mechanism of the present invention, shown by way of example as embodiments of the probe 10, 100, 110, 120, 130 and 140, may occur to those skilled in the art upon reviewing the subject matter of this invention. Such variations, if within the spirit of this disclosure, are intended to be encompassed within the scope of this invention. The description of the embodiments as set forth herein, and as shown in the drawings, is provided for illustrative purposes only and, unless otherwise expressly set forth, is not intended to limit the scope of the claims, which set forth the metes and bounds of my invention. Accordingly, all matter contained in the above description or shown in the accompanying drawings should be interpreted as illustrative and not in a limiting sense.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

What is claimed is:

1. An electronic visual food probe for insertion into an interior portion of a body of food being cooked to provide a color image of a cross-section of said interior portion proximate said probe, said food probe comprising:

a. a substantially rigid stem having a proximal end and a distal end opposite said proximal end, said stem distal end having an outer sidewall;
b. an elongated inner chamber generally extending lengthwise through at least a portion of the stem distal end, said elongated inner chamber being encased at least in part by said outer sidewall;
c. an elongated opening in said outer sidewall, said elongated opening generally being oriented lengthwise along at least a portion of the stem distal end and having a length of at least one-half inch, said elongated opening penetrating from said outer sidewall into said elongated inner chamber;
d. a window positioned at least in part in said elongated opening, said window being at least in part translucent or transparent;
e. a light source, said light source generating light and projecting said light external to the stem and against the interior portion of said body of food proximate the elongated opening so as to create an illuminated region of said inner portion of said body of food visible from said elongated opening;
f. a first optic element positioned proximate said elongated opening so as to receive reflected light from at least an elongated segment of said illuminated region of said body of food through said elongated opening, said elongated segment being at least one-half inch long, said first optic element being shaped, positioned and adapted to convey from said reflected light a strip-shaped color image indicative of at least a one-half inch length of said elongated segment;
g. a first optic conduit positioned at least in part in the stem, said first optic conduit having a proximal end and a distal end opposite the proximal end, said first optic conduit having a light transmitting core between said proximal and distal ends, the distal end of the first optic conduit receiving the strip-shaped optic color image from said first optic element, said first optic conduit channeling said strip-shaped color image through its said transmitting core to and through its said proximal end;
h. an electronic image sensor positioned proximate the proximal end of the first optic conduit, said electronic image sensor receiving the strip-shaped color image from said proximal end of said first optic conduit and generating electronic data indicative of said strip-shaped color image; and
i. an electronic display system comprising a computer processor and an electronic display, said computer processor receiving the electronic data from the electronic image sensor, converting the electronic data into an electronically displayable image indicative of the strip-shaped color image, and displaying said displayable image on the electronic display.

2. The electronic visual food probe of claim 1, further comprising a second optic conduit positioned at least in part in the stem, said second optic conduit having a proximal end and a distal end opposite the proximal end, said second optic conduit having a light transmitting core between said proximal and distal ends, said distal end positioned proximate the elongated opening, said proximal end positioned proximate said light source, said second optic conduit receiving light from said light source through said second optic conduit's said proximal end and channeling said light through its said light transmitting core to and through its said distal end to create said illuminated region of said body of food.

3. The electronic visual food probe of claim 1, wherein said first optic element comprises one of a light admitting optic face, a mirror, an optic lens, a compound optic lens, a diffraction optic, a collection of micro optic lenses, and an array of optic lenses.

4. The electronic visual food probe of claim 1, wherein when the stem is inserted to a desired position within said interior portion of said body of food, said first optic element is adapted to receive and convey said strip-shaped color image without having to reposition the stem from said desired position.

5. The electronic visual food probe of claim 1, wherein one of said first optic element and said distal end of said first optic conduit, is fixedly positioned relative to the elongated opening.

6. The electronic visual food probe of claim 1, wherein said elongated opening has an elongated insertion portion, said elongated insertion portion comprising the length of said elongated opening inserted into said body of food, said electronic display system truncating said electronically displayable image so as to display no more of said elongated opening than said elongated insertion portion.

7. The electronic visual food probe of claim 1, further comprising a wireless transmitter and a wireless receiver, said wireless transmitter wirelessly communicating said electronic data from said wireless transmitter to said wireless receiver.

8. The electronic visual food probe of claim 1, wherein said first optic element comprises at least in part said window.

9. An electronic visual food probe for insertion into an interior portion of a body of food being cooked to provide a color image of a cross-section of said interior portion proximate said probe, said food probe comprising:
a. a substantially rigid stem, said stem having a proximal end and a distal end opposite said proximal end;
b. a light source, said light source generating illumination light to illuminate said cross-section of said interior portion of said body of food proximate said stem distal end;
c. a first optic element, said first optic element being shaped and positioned relative to said stem distal end to receive reflected light from said illuminated region proximate said stem distal end and to convey from said reflected light a strip-shaped color image indicative of an elongated segment of said illuminated region, said elongated segment having a length of at least one-half inch;
d. a first optic conduit attached to the stem, said first optic conduit having a proximal end and a distal end opposite the proximal end, said first optic conduit distal end being positioned proximate said stem distal end and proximate said first optic element, said first optic conduit having an elongate light transmitting core between its said proximal and distal ends, said first optic conduit receiving said strip-shaped color image from said first optic element through said first optic conduit's said distal end, directing said strip-shaped color image through its said transmitting core and emitting said strip-shaped color image out of its said proximal end;
e. an electronic image sensor positioned proximate the first optic conduit proximal end, said electronic image sensor receiving the strip-shaped color image from said proximal end of said first optic conduit, said electronic image sensor generating electronic data indicative of said strip-shaped color image; and f. an electronic display system comprising a computer processor and an electronic display, said computer processor receiving the electronic data from the electronic image sensor, converting the electronic data into an electronically displayable image indicative of the strip-shaped color image, and displaying said displayable image on the electronic display;

wherein said stem distal end comprises an inner cavity and an elongated opening, said inner cavity housing at least in part said first optic conduit and housing at least in part said first optic element, said elongated opening extending lengthwise along the side of said stem distal end and penetrating into said inner cavity, said elongated opening being at least one-half inch long and having a window positioned at least in part in said elongated opening, said window being at least in part translucent or transparent, said first optic element being shaped and positioned to collect reflected light from said illuminated region through said elongated opening and convey from said reflected light said strip-shaped color image.

10. The electronic visual food probe of claim 9, wherein said first optic element comprises one of a light admitting optic face, a mirror, an optic lens, a compound optic lens, a diffraction optic, a collection of micro optic lenses, and an array of optic lenses.

11. The electronic visual food probe of claim 9, further comprising a second optic conduit, said second optic conduit having a proximal end and a distal end opposite the proximal end, said second optic conduit having an elongate light transmitting core between the proximal and distal ends, said second optic conduit proximal end positioned proximate and collecting illumination light generated by said light source, said second optic conduit distal end positioned proximate the distal end of the stem, said second optic conduit directing said illumination light through its said transmitting core to and out its said distal end, said distal end being oriented to direct said illumination light against the interior portion of said body of food proximate the stem so as to create said illuminated region when said stem is inserted into said body of food.

12. The electronic visual food probe of claim 11, wherein said second optical conduit comprises a substantially rigid portion that forms at least in part said stem.

13. The electronic visual food probe of claim 9, wherein one of said first optic element and said first optic conduit distal end is fixedly positioned relative to the elongated opening.

14. The electronic visual food probe of claim 9, wherein said first optical conduit comprises a substantially rigid portion that forms at least in part said stem.

15. The electronic visual food probe of claim 9, further comprising a temperature sensor proximate the elongated opening, said temperature sensor sensing the temperature in proximity to the elongated opening and communicating an electronic signal indicative of the temperature sensed by the temperature sensor to the electronic display system, the electronic display system being adapted to present information on the electronic display indicative of the temperature sensed by the temperature sensor.

16. The electronic visual food probe of claim 9, wherein said first optic conduit comprises one of a fiber optic cable and a hollow chamber.

17. The electronic visual food probe of claim 9, wherein said first optic element is shaped and positioned relative to said elongated opening to cause said strip-shaped color image to substantially correspond in shape to said elongated opening.

18. The electronic visual food probe of claim 9, wherein said elongated opening has an elongated insertion portion, said elongated insertion portion comprising the length of said elongated opening inserted into said body of food, said electronic display system truncating said electronically displayable image so as to display no more of said elongated opening than said elongated insertion portion.

19. The electronic visual food probe of claim 9, further comprising a wireless transmitter and a wireless receiver, said wireless transmitter wirelessly communicating said electronic data from said wireless transmitter to said wireless receiver.

20. The electronic visual food probe of claim 9, wherein said first optic element comprises at least in part said window.

* * * * *